United States Patent
Kelly

(10) Patent No.: US 7,320,801 B2
(45) Date of Patent: Jan. 22, 2008

(54) PATCH FOR TREATING SYMPTOMS OF A SKIN ABSCESS

(76) Inventor: Jack Perez Kelly, 105 Fischer Dr., Pearl River, LA (US) 70452

( * ) Notice: Subject to any disclaimer, the term of this patent is extended or adjusted under 35 U.S.C. 154(b) by 45 days.

(21) Appl. No.: 11/236,264

(22) Filed: Sep. 26, 2005

(65) Prior Publication Data

US 2007/0071801 A1 Mar. 29, 2007

(51) Int. Cl.
*A61L 15/16* (2006.01)
*A61F 5/44* (2006.01)

(52) U.S. Cl. ...................... 424/447; 604/355

(58) Field of Classification Search ........... 424/445, 424/446, 447–449; 604/355, 367, 378, 346, 604/347, 349; 602/48, 57
See application file for complete search history.

(56) References Cited

U.S. PATENT DOCUMENTS

| | | | | |
|---|---|---|---|---|
| 1,862,122 | A * | 6/1932 | Schrader | 604/307 |
| 2,221,758 | A * | 11/1940 | Elmquist | 128/888 |
| 2,443,140 | A * | 6/1948 | Larsen | 128/888 |
| 2,807,262 | A * | 9/1957 | Lew | 602/47 |
| 2,937,971 | A | 5/1960 | Shackell | |
| 3,580,254 | A * | 5/1971 | Stuart | 604/290 |
| 3,814,095 | A * | 6/1974 | Lubens | 604/307 |
| 3,912,667 | A | 10/1975 | Spitzer | |
| 4,560,549 | A * | 12/1985 | Ritchey | 424/431 |
| 4,666,441 | A * | 5/1987 | Andriola et al. | 424/448 |
| 4,890,608 | A * | 1/1990 | Steer | 602/57 |
| 4,917,688 | A * | 4/1990 | Nelson et al. | 604/306 |
| 4,994,049 | A * | 2/1991 | Latzke et al. | 604/307 |
| 5,264,218 | A * | 11/1993 | Rogozinski | 424/445 |
| 5,683,354 | A * | 11/1997 | Levy | 602/54 |
| 6,685,682 | B1 * | 2/2004 | Heinecke et al. | 604/307 |
| 6,940,000 | B1 * | 9/2005 | Davis | 602/42 |
| 6,987,209 | B2 * | 1/2006 | Augustine et al. | 602/42 |
| 7,135,606 | B1 * | 11/2006 | Dozier et al. | 602/57 |
| 2002/0197284 | A1 | 12/2002 | Luo et al. | |
| 2003/0077316 | A1 | 4/2003 | Nichols et al. | |
| 2003/0092754 | A1 | 5/2003 | Nishimuta et al. | |
| 2003/0113356 | A1 | 6/2003 | Deckner et al. | |
| 2004/0241215 | A1 | 12/2004 | Lipman | |
| 2005/0129744 | A1 | 6/2005 | Caldwell et al. | |

* cited by examiner

*Primary Examiner*—Sharon Kennedy
(74) *Attorney, Agent, or Firm*—Keaty Professional Law Corporation

(57) ABSTRACT

A patch, or bandage for treating skin infections has a backing with pressure-sensitive adhesive for securing on a user's skin in the area of the boil. A liquid absorbent member is positioned in the center of the patch, while a carrier with a medicinal formulation, comprising a menthol solution, surrounds the absorbent member. The medicinal substance is covered with one or more concentric removable covers, which are peeled off depending on the size of the boil. The menthol solution forms a barrier preventing bacteria from expanding the boil. Once the boil drains, the exudates is absorbed by the absorbent member.

22 Claims, 2 Drawing Sheets

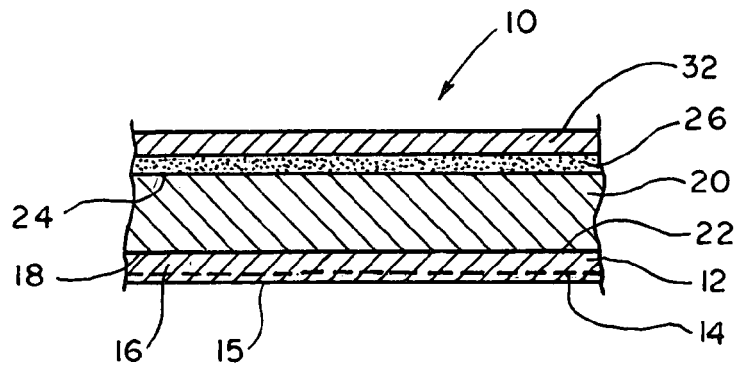
F I G. 4
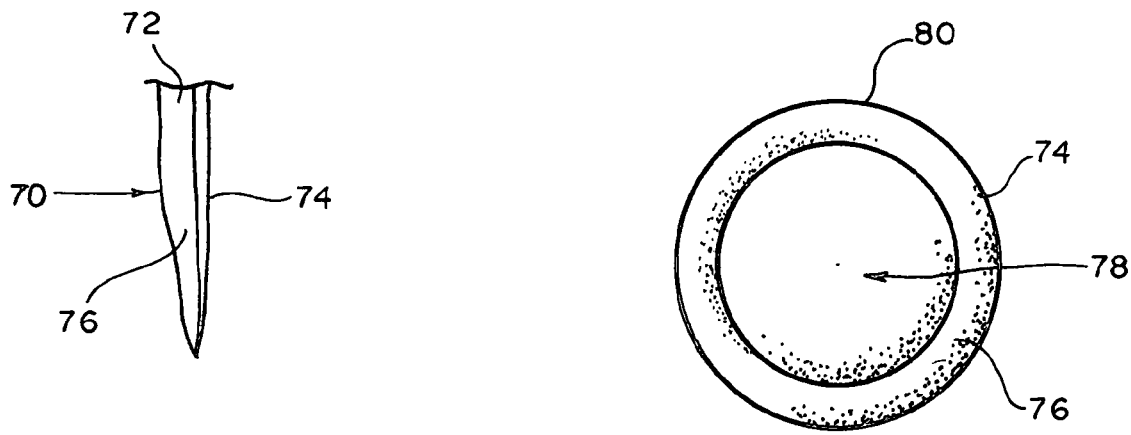
F I G. 5
F I G. 6
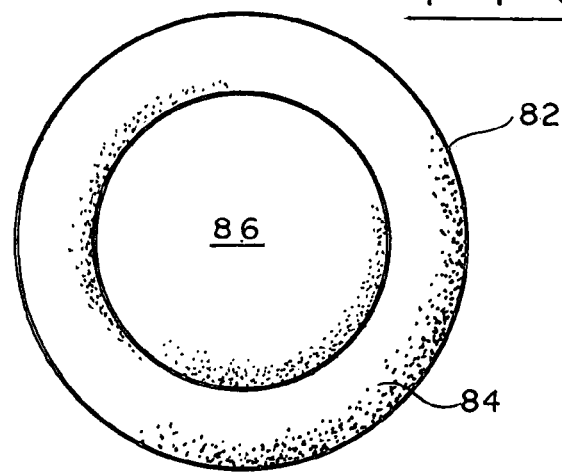
F I G. 7

PATCH FOR TREATING SYMPTOMS OF A SKIN ABSCESS

BACKGROUND OF THE INVENTION

The present invention relates to a bandage, more specifically to bandage which carries a topical agent to facilitate treatment of a skin abscess.

An abscess is a pocket of pus that forms at the site of infected tissue. An abscess can form on the skin or on tissues within the body and cause pain, swelling, and tenderness. Bacteria are a common cause of the infections that form abscesses. A skin abscess can be caused by infection from venomous insect bites, ingrown hair follicles, or bacterial illnesses such as staphylococcus aureus infection. Methicillin-resistant *Staphylococcus Aureus* (MRSA) is an antibiotic resistant staff infection that is common in health care facilities. A symptom of MRSA, along with other staphylococcus infections, is the presence of skin abscesses.

Depending on the size and location of the abscess, doctors suggest treating the abscess by using a needle to drain it, or cutting open the abscess to remove the pus and infectious material, or prescribe antibiotics (pills or a shot). This may be adequate treatment if the abscess is extremely small and treatment is not delayed. Often times, healthcare professionals suggest applying heat packs or hot water soaking of the affected area to cause localizing of the abscess and promote drainage. Once the abscess becomes soft or "forms a head," it can be drained. A bandage is often placed over the boil in order to protect it and prevent contact pain of the skin with clothes.

Sometimes, especially with larger skin abscesses, the abscess will need to be drained or "lanced" by a healthcare practitioner. Frequently, these abscesses contain several pockets of white blood cells, antibodies, and infection that must be opened and drained.

While hot soaks can be done in almost any condition, lancing of the skin requires a skilled person, who may not be immediately available to the patient.

The present invention contemplates a bandage which uses a medicated patch in order to drive the infection associated with a skin abscess to the center and induces the abscess to form a head which drains without assistance from a healthcare provider.

SUMMARY OF THE INVENTION

It is, therefore, an object of the present invention to provide a medicated bandage, or patch for positioning on the patient's skin in the area of a skin abscess.

It is another object of the present invention to provide a medicated patch to facilitate absorption of a skin abscess exudate while protecting the skin surrounding the treatment area.

It is a further object of the present invention to provide a medicated skin patch with self-adhesive substrate to facilitate retention of the patch in the area of skin abscess.

These and other objects of the present invention are achieved through a provision of an adhesive patch device, which comprises a flexible substrate with an adhesive material for positioning on a user's skin, a liquid absorbent member positioned in a juxtaposed position on the substrate and a therapeutic formulation surrounding the absorbent member. The therapeutic formulation comprises an anesthetic, counterirritant, antifungal, antibacterial substances, for instance menthol, or 10% menthol solution. The therapeutic substance may be deposited as a layer on a carrier, or a carrier may be provided impregnated with the medicinal substance. The carrier is secured to the substrate and can have the same dimensions as the absorbent member, being interposed between the substrate and the absorbent member.

One or more removable cover members cover the medicinal layer; the covers may removed one at a time to surround the skin abscess. Depending on the size of the abscess, one or more covers are removed so that the center of the skin abscess is surrounded with the therapeutic formulation. Once the boil drains, the exudates is absorbed by the absorbent member, preventing contamination of the surrounding skin tissue.

BRIEF DESCRIPTION OF THE DRAWINGS

Reference will now be made to the drawings, wherein like parts are designated by like numerals, and wherein

FIG. 4 is a cross-sectional view taken along lines 4-4 of FIG. 3.

FIG. 5 is a side end view of a third embodiment of the present invention showing a circular patch with a single medicated ring.

FIG. 6 is a front view of the third embodiment.

FIG. 7 is a plan view of an outer bandage portion designed to be placed over the medicated ring.

DETAIL DESCRIPTION OF THE PREFERRED EMBODIMENTS

Figure 1:
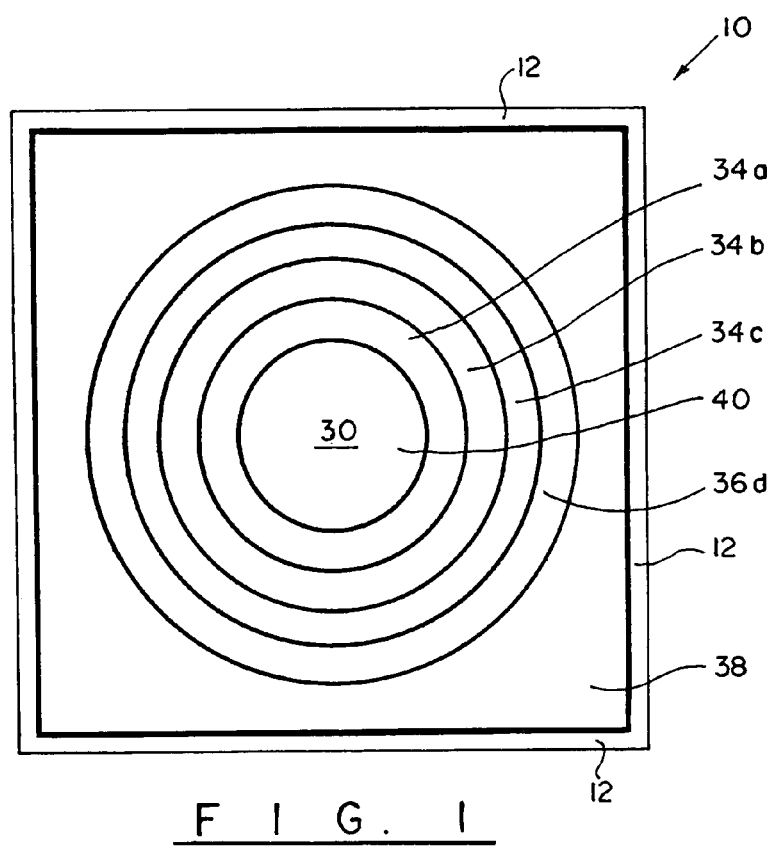
FIG. 1 is a top view of the bandage, or patch according to the first embodiment of the present invention.

Turning now to the drawings in more detail, numeral 10 designates the medicated bandage, or patch in accordance with the present invention. The patch 10 comprises a self-adherent elastic substrate 12, which has a coating 14 of pressure-sensitive adhesive material deposited on a first surface 16 of the substrate 12. The first surface 16 is adapted to directly contact the skin of the user when the patch 10 is positioned in an area of a skin abscess or boil. This contact allows the patch 10 to remain in place and prevents sliding or shifting of the bandage 10 after it is in place. The adhesive may be applied in various patterns including random patterns, if desired.

The adhesive coating 14 may be one of the known, readily adhering self-adhesive compositions based on rubber or on synthetic polymers. The coating 14 compositions advantageously have good skin compatibility. If desired, an adhesion promoter can also be deposited on the surface 16 beneath the adhesive coating 14. The self-adhesive coating 14 is normally covered with a sheet of backing 15, which is peeled off immediately prior to positioning of the patch 10 on the user's skin. The backing 15 may be given an anti-adhesive finish, such as, for example, siliconized paper or plastic film to facilitate easy removal of the backing 15 from the substrate 12.

A second surface 18 of the substrate 12 is fused to a non-woven carrier layer 20, which is formed from a flexible, porous material, for instance open-cell foam. The open cell foam comprises polyurethane, polyvinyl chloride, polyethylene, or any combination thereof.

The carrier 20 has a first surface 22, which is fused to the surface 18 of the substrate 12 and a second surface 24. A coating of therapeutic, medicinal material 26 is deposited on the second surface 24, extending in a circular pattern about a center 30 of the patch 10. In the preferred embodiment, the medicinal coating 26 is selected from a group consisting of anesthetic, counterirritant, antifungal substances, for instance menthol, or 10% menthol solution. Menthol, chemical formula $CH_3C_6H_9(C_3H_7)OH$, is a crystalline organic chemical which is produced from peppermint plants and can also be artificially produced from coal tar. Menthol is also noted to have antibiotic properties. Alternatively, the foam layer 20 may be impregnated with the anesthetic, antifungal, counterirritant, antibiotic substance, such as menthol. The medicinal substance of the coating may also comprise between 1% to 15% methyl silicylate. The medicinal coating may also comprise between 0.01% to 5% of wintergeen oil, which contains methyl salicylate and gaultherilene.

A protective cover layer 32 is positioned over the medicinal coating 26. The cover layer 32 comprises one or more concentric cover members, or portions 34, which surround the center 30 of the patch 10. Each cover portion 34a-34d is separately positioned over the coating 26 and can be peeled off separately, depending on the size of the skin abscess. The cover layer 32 also comprises a peripheral portion 38, which extends about the periphery of the patch 10 without extending outside of the substrate 12. The peripheral portion 38 usually remains in place, covering the medicinal coating 26 and is not peeled off during use. Of course, if desired the peripheral portion 38 can also be removed to expose the medicinal layer 26.

An absorbent member 40 is positioned in the center of the patch 10 and is fused or otherwise secured to the carrier layer 20. The absorbent material both absorbs the abscess exudate (which is usually bacteria-filled pus) and protects the skin abscess by absorbing shock of contact with solid objects. A variety of materials may be used as the absorbent layer in this invention, for instance foams, woven or nonwoven materials, such as cotton, rayon, polyester, polyurethane, polyolefin, cellulose, cellulose derivatives, nylon, and the like. Other types of materials having similar absorbent properties and characteristics would also be suitable for use in this invention. A preferred absorbent layer is a woven or nonwoven material of natural or synthetic fibers made from, but not limited to, cotton, polyester, rayon, polyurethane, polyolefin, cellulose, cellulose derivatives, or nylon. Also, hydrogel polymeric materials may be used, if desired.

The absorbent member 40 is sized to cover at least a center of the skin abscess, which is usually red and tender. As the skin abscess becomes centralized, the bacteria concentrates at the very center of the abscess. The medicinal substance 26 tends to localize the abscess and facilitate its concentration in the center. Eventually, the abscess bursts and exudes the puss. The absorbent member 40 is designed to absorb the exudate and prevent its movement to the skin areas surrounding the boil.

Figure 2:
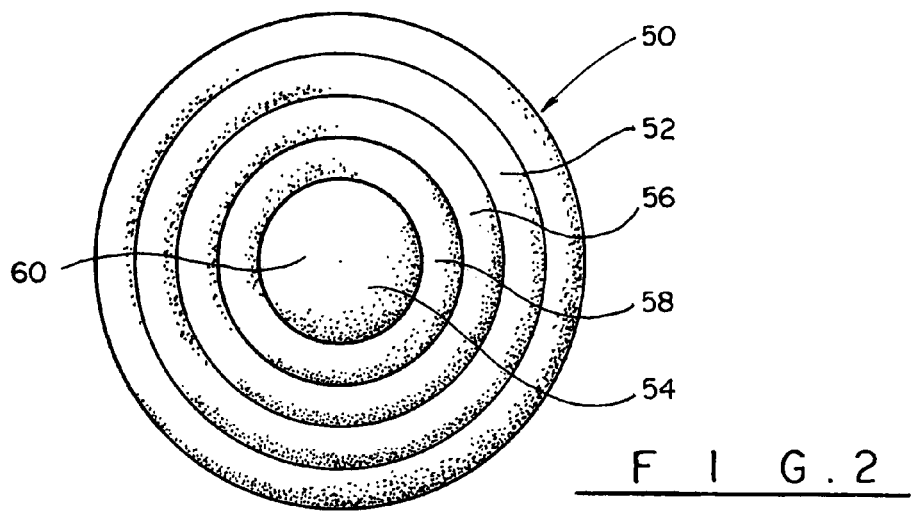
FIG. 2 is a top view of the bandage, or patch according to the second embodiment of the present invention.
Figure 3:
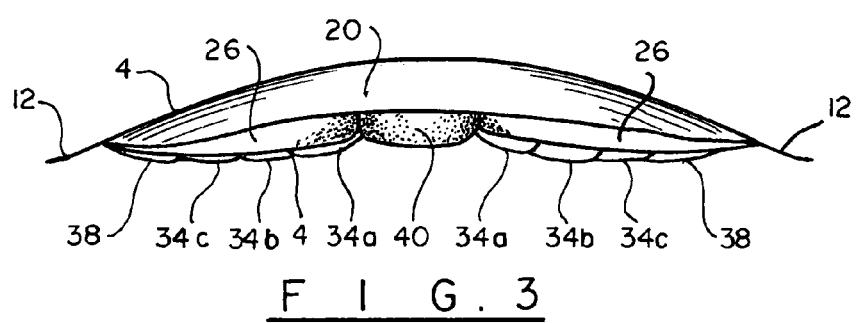
FIG. 3 is an end view of the patch in accordance with the present invention.

Turning now to the embodiment of FIG. 2, the medicated patch 50 is shown to comprise an adhesive substrate 52, which is shaped as a circle. The design of the patch 50 is structurally analogous although not 'identical to the design of the patch 10. Similarly to the embodiment of FIG. 1, the patch 50 has an absorbent member 54. However, in this embodiment, the flexible porous absorbent member 54 covers a greater surface and may extend from an outer ring 58.

The medicated substance, similar to the layer 26, is deposited on the absorbent member 54 in the area protected by the removable ring 56 and a removable ring 58. In the alternative, the absorbent layer 54 is impregnated with the medicinal substance in the areas covered by the removable, peel-off cover rings 56 and 58. The very center 60 of the absorbent member 54 is free from the medicinal substance, allowing the abscess to be concentrated and erupted while protected by the patch 50.

FIGS. 5-7 illustrate a third embodiment of the patch in accordance with the present invention. In this embodiment, the bandage 70 comprises a foam carrier layer 72 having a first side 74 carrying an adhesive coating. The second side of the carrier 72 is covered with a medicated substance, which forms a layer 76. The medicine-free area 78 occupies the center of the patch 70. A removable peel-off ring 80 covers the medicated layer 76. The ring 80 is removed immediately prior to positioning of the patch 70 on the skin.

The outer elastic bandage portion 82 is sized and shaped to be placed over the medicated patch 70. The outer bandage portion 82 comprises an outer ring 84, which is sized to extend outside of the circumference of the ring 74. The adhesive coating allows the ring 84 to be secured to the patch 70 and to the patient's skin. The inner absorbent area 86 is sized and configured to be placed over the side 74 of the patch 70 and adhere thereto, thereby securing the outer bandage portion 82 to the patch 70.

As with the patches 10 and 50, the center area 78, which is intended to rest against the abscess area is preferably made nonadherent to the skin surface, otherwise fibers might be left behind on the skin, causing discomfort and the patient. If desired the elastic layers that affix the patches to the skin be formed from elastomeric material that is breathable and porous or made from stretchable fabric web. Of course, the size of the medicated patches of the present invention can very depending on the size of the abscesses they are designed to treat.

In operation, depending on the size of the abscess, the user peels off one or more protective ring covers to expose the medicated substance, bearing in mind that the medicated ring should fit around the outside of the site of infection only. The user then peels off the backing to expose the adhesive and presses the adhesive layer to the skin, securing the patch on the skin. Care should be taken not to cover the center of the boil. After 6-8 hours, the patch may be removed, and the skin area soaked in warm water to facilitate abscess concentration. If necessary another patch may be applied after the air circulated on the skin and the skin is sufficiently dry.

Then another patch may be positioned on the skin, and the application repeated until the trapped infection drains through the skin. In some tests, it was observed that the boil begins to drain after two-three days of the application. The medicated substance forms an impassible barrier between the center of the patches and the area permeated with the menthol solution. The antiseptic layer will contain the infection within the center and cause it to drain. The rings covering the medicinal substance can be peeled off individually to make the area of the skin which is not exposed to the medicated substance as large or as small as necessary, which will allow the bandage to accommodate various size skin abscesses.

Many changes and modifications can be made in the design of the present invention without departing from the spirit thereof. I, therefore, pray that my rights to the present invention be limited only by the scope of the appended claims.

I claim:

1. An adhesive patch device comprising a flexible substrate with an adhesive material for positioning on a user's skin, a liquid absorbent member positioned in a juxtaposed position on the substrate and a medicinal substance disposed in a circular pattern about a center of the patch such that the medicinal substance can be delivered to areas of the user's skin surrounding the absorbent member.

2. The device of claim 1, wherein said medicinal substance is deposited onto a flexible carrier secured to the substrate.

3. The device of claim 1, further comprising at least one cover member detachably positioned in a covering relationship over said medicinal substance, said at least one cover member surrounding said absorbent member.

4. The device of claim 2, wherein said carrier extends between the substrate and the medicinal substance.

5. The device of claim 2, wherein said carrier is impregnated with the medicinal substance.

6. The device of claim 2, wherein said carrier surrounds said absorbent member.

7. The device of claim 2, wherein said substrate has a surface area, which is at least slightly greater than the surface area of the carrier.

8. The device of claim 1, wherein said absorbent member is formed from woven or non-woven absorbent material.

9. The device of claim 1, wherein said medicinal substance is selected from the group consisting of anesthetic, counterirritant, antifungal, antibacterial agents.

10. The device of claim 1, wherein said medicinal substance comprises a menthol solution.

11. The device of claim 1, wherein said adhesive material is a pressure-sensitive adhesive material.

12. The device of claim 1, wherein said substrate has a generally rectangular configuration.

13. The device of claim 1, wherein said substrate has a generally circular configuration.

14. An adhesive patch device comprising a flexible substrate with an adhesive material for positioning on a user's skin, a liquid absorbent member positioned in a juxtaposed position on the substrate and a medicinal substance disposed in a circular pattern about a center of the patch, said medicinal substance being delivered to areas of the user's skin surrounding the absorbent member, said device further comprising a plurality of concentric cover members, each of the cover member being separately detachably positioned in a covering relationship over said medicinal substance, an innermost of said cover members being disposed in a surrounding relationship in relation to the absorbent member.

15. A skin bandage device, comprising a flexible substrate, the substrate having a front side oriented toward the user's skin when the device is positioned on the user's skin and a back side oriented away from the user's skin, a therapeutic formulation positioned on at least a portion of the front side, a detachable cover member for covering the therapeutic formulation, and an absorbent member positioned inwardly in relation to the user's skin, wherein the therapeutic formulation comprises a menthol solution, said therapeutic formulation being disposed in a circular pattern about a center of the patch such that the therapeutic formulation can be delivered to areas of the user's skin surrounding the absorbent layer.

16. The device of claim 15, further comprising a means for securing the substrate on the user's skin.

17. The device of claim 16, wherein said securing means comprises a flexible backing having a pressure-sensitive adhesive deposited on an outer surface and a pressure-sensitive adhesive deposited on an inner surface, said inner surface being adapted for engagement with the substrate, and said outer surface is being adapted for contacting the user's skin.

18. The device of claim 15, wherein said therapeutic formulation surrounds the absorbent member.

19. The device of claim 15, further comprising at least one cover member detachably positioned in a covering relationship over said therapeutic formulation.

20. A method of treating a skin abscess, comprising the steps of:
  a. providing an adhesive patch device comprising a flexible substrate with an adhesive material for positioning on a user's skin, a liquid absorbent member positioned in a juxtaposed position on the substrate, a therapeutic material disposed adjacent to periphery of the absorbent member, and at least one cover member detachably positioned over the therapeutic material;
  b. removing the cover member and exposing the therapeutic material;
  c. positioning the patch in the selected location of the skin abscess, while contacting the absorbent member with an imaginary center of the skin abscess;
  d. securing the substrate on the user's skin such that the exposed therapeutic material generally surrounds the imaginary center of the skin abscess.

21. The method of claim 20, comprising the steps of repeating steps a. through d. of claim 20 until such time as the skin abscess drains and exudate is absorbed in the absorbent member.

22. The method of claim 20, further comprising the step of providing a carrier for retaining said therapeutic material on said substrate.

* * * * *